United States Patent
Bharj

(10) Patent No.: US 10,092,225 B2
(45) Date of Patent: Oct. 9, 2018

(54) NON-INVASIVE SYSTEM AND METHOD FOR MEASURING BLOOD GLUCOSE IN THE HUMAN BODY UTILIZING A MODIFIED CERAMIC COAXIAL RESONATOR

(71) Applicant: Sarijit S. Bharj, Hamilton, NJ (US)

(72) Inventor: Sarijit S. Bharj, Hamilton, NJ (US)

( * ) Notice: Subject to any disclaimer, the term of this patent is extended or adjusted under 35 U.S.C. 154(b) by 420 days.

(21) Appl. No.: 15/043,454

(22) Filed: Feb. 12, 2016

(65) Prior Publication Data
US 2017/0231536 A1    Aug. 17, 2017

(51) Int. Cl.
*A61B 5/145*    (2006.01)
*A61M 5/142*    (2006.01)
*A61M 5/172*    (2006.01)
*A61B 5/00*     (2006.01)

(52) U.S. Cl.
CPC ........ *A61B 5/14532* (2013.01); *A61B 5/6826* (2013.01); *A61B 5/742* (2013.01); *A61M 5/14244* (2013.01); *A61M 5/1723* (2013.01); *A61M 2005/1726* (2013.01)

(58) Field of Classification Search
CPC ............ A61M 5/14244; A61M 5/1723; A61M 2005/1726; A61B 5/14532; A61B 5/742; A61B 5/6826; A61B 5/145; A61B 2562/0223; A61B 2562/0228
See application file for complete search history.

(56) References Cited

U.S. PATENT DOCUMENTS

| | | | |
|---|---|---|---|
| 5,700,745 A * | 12/1997 | Okuyama | ............... C04B 35/49 501/134 |
| 6,762,142 B2 * | 7/2004 | Okuyama | ............... C04B 35/49 501/134 |
| 9,078,606 B1 | 7/2015 | Bharj | |
| 2010/0112614 A1 | 5/2010 | Axelrod | |
| 2016/0338624 A1 * | 11/2016 | Min | ................... A61B 5/14532 |

* cited by examiner

*Primary Examiner* — Eric Winakur
(74) *Attorney, Agent, or Firm* — LaHorte & Associates, P.C.

(57) ABSTRACT

A system and method for measuring glucose levels in a user's blood without having to draw a blood sample. A wave energy source emits wave energy. A modified ceramic coaxial resonator is provided that receives the wave energy and produces a frequency oscillation. An opening is formed in a conductive layer surrounding the ceramic coaxial resonator. Skin tissue is pressed against the opening. The sample tissue alters the frequency oscillation created by the ceramic coaxial resonator. At least some of the altered frequency oscillation is indicative of blood glucose levels within the sample tissue.

18 Claims, 9 Drawing Sheets

NON-INVASIVE SYSTEM AND METHOD FOR MEASURING BLOOD GLUCOSE IN THE HUMAN BODY UTILIZING A MODIFIED CERAMIC COAXIAL RESONATOR

BACKGROUND OF INVENTION

1. Field of the Invention

In general, this invention relates to blood glucose measuring devices and techniques. More particularly, this invention relates to systems and methods that can measure blood glucose in the body without the need to draw a blood sample.

2. Prior Art Description

Diabetes is a chronic disease without a cure. Over twenty five million people in the United States of America have diabetes. Diabetes is the seventh leading cause of death in the United States. Currently, diabetes is estimated to cost the United States health care system over one-hundred billion dollars annually.

Diabetes creates high blood glucose levels due to a deficiency of insulin production and action. This failure leads to hyperglycemia. Persistent hyperglycemia causes a variety of serious symptoms and life threatening long term complications such as dehydration, diabetic coma, cardiovascular disease, and poor blood circulation.

Many diabetics are required to take insulin in order to control the glucose levels in their blood. However, having insulin levels in the blood that are too high are just as dangerous as having insulin levels in the blood that are too low. Consequently, it is critical that diabetics who use insulin precisely monitor the level of glucose in their bodies.

The most common and accurate glucose monitoring techniques require that a blood sample be drawn from the body. This is typically done by pricking the skin with a needle or lancet to obtain a small droplet of blood. The blood is placed upon a chemically treated strip of paper. The strip of paper is then placed in a glucometer, which tests the blood and provides a glucose level reading.

Pricking the skin can be painful. Areas of the skin can also experience increased sensitivity to pain if those areas are repeatedly pricked over long periods of time. Furthermore, many diabetics have blood circulation problems. As a result, these diabetics can only draw blood from certain parts of the body, such as the fingertips, where good blood flow remains. Unfortunately, the areas of the body that have good blood flow often correspond to the areas of the body that have a high concentration of nerve endings, thus increasing the pain associated with obtaining such a blood sample. The result often is that diabetics are deterred from testing and consequently test their blood glucose levels far less often than they should.

For the reasons stated above, there has been a long standing need for a glucose monitoring device that can detect the level of glucose in a diabetic without the need for a drawn blood sample. In the prior art, certain devices have been produced that claim that they can meet this need. For instance, in U.S. Patent App. Pub. No. 2010/0112614 to Axelrod, entitled Coupled Antenna Impedance Spectroscopy, a methodology is presented for measuring blood glucose levels. However, the technique does not produce accurate results in comparison to common blood drawn testing techniques. More importantly, such methodologies require the use of a spectroscope. Consequently, such testing systems are limited to use in hospitals and labs that have spectroscopes. Such testing systems cannot be made into low-cost portable devices using known technologies.

In U.S. Pat. No. 9,078,606, to Bharj, the Applicant presented an earlier design for a passive glucose monitoring system that measures blood glucose levels using a microwave resonance chamber. However, in order for the system to function properly, a mass of skin has to be pressed against a hole in the microwave resonance chamber so that some of the skin and body tissue bulges through the hole and into the microwave resonance chamber. This requirement mandates that the resonance chamber be relatively large in order to receive the tissue needed for an accurate test. As such, the system cannot be miniaturized to any significant degree without causing adverse affects to the monitoring accuracy.

Many diabetics carry insulin pumps that automatically pump insulin into the bloodstream at a selected rate. Insulin pump systems are designed to be as small and discrete as possible so that the systems can be comfortably worn without being seen. Insulin pump systems typically rely upon a person's average blood sugar levels, as monitored over time. The problem is that many diabetics fluctuate from their averages as they rest, exercise, eat, and drink. Insulin pumps can be made much more effective if the system were capable of constantly monitoring blood sugar levels in real time. In this manner, the system could inject insulin only when insulin was needed. To monitor blood levels in this manner, a passive blood monitoring system is required that does not require blood contact and can be made small enough so as to not to increase the size of insulin pumps to any significant degree.

This need is met by the present invention as described and claimed below.

SUMMARY OF THE INVENTION

The present invention is a system and method for measuring glucose levels in a user's blood without having to draw a blood sample. Rather, the glucose level of the blood is tested in a non-invasive manner through the skin using RF energy waves in the ISM frequency bands that are passed through a modified ceramic coaxial resonator. To test a user's blood, an RF electromagnetic (EM) energy source is provided that has an RF source frequency. The RF source frequency is determined by the modified ceramic coaxial resonator. The RF source frequency is selected to be a quarter wavelength, or odd multiple wavelength, of the modified ceramic coaxial resonator being used. The modified ceramic coaxial resonator has a central hollow surrounded by a body of dielectric material that can have a square or round cross-section. The dielectric material is covered with a conductive sheathing. One or more slots are formed in the conductive sheathing that exposes the dielectric material.

The wave energy source causes the modified ceramic coaxial resonator to produce a frequency oscillation. Contact of skin tissue with the dielectric material exposed in the slot on the modified ceramic coaxial resonator alters the frequency oscillation in correlation to glucose levels in the skin and surrounding tissue.

Circuitry is provided that converts the frequency oscillation into a display signal. As such, glucose levels can be read instantly and/or continuously from the display after merely touching the modified ceramic coaxial resonator with a segment of skin that has blood tissue underneath. No drawing of blood is required.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE INVENTION

In the following detailed description, numerous specific details are set forth to provide a thorough understanding of the invention. However, it will be understood by those skilled in the art that the present invention may be practiced without these specific details. References to the invention described are for illustrations and understanding and should not be taken as limiting.

Although the present invention glucose monitoring sensor and system can be embodied in many ways, only a few embodiments of the sensor and system have been selected for illustration and discussion. The illustrated embodiments, however, are merely exemplary and should not be considered a limitation when interpreting the scope of the claims.

Figure 1:
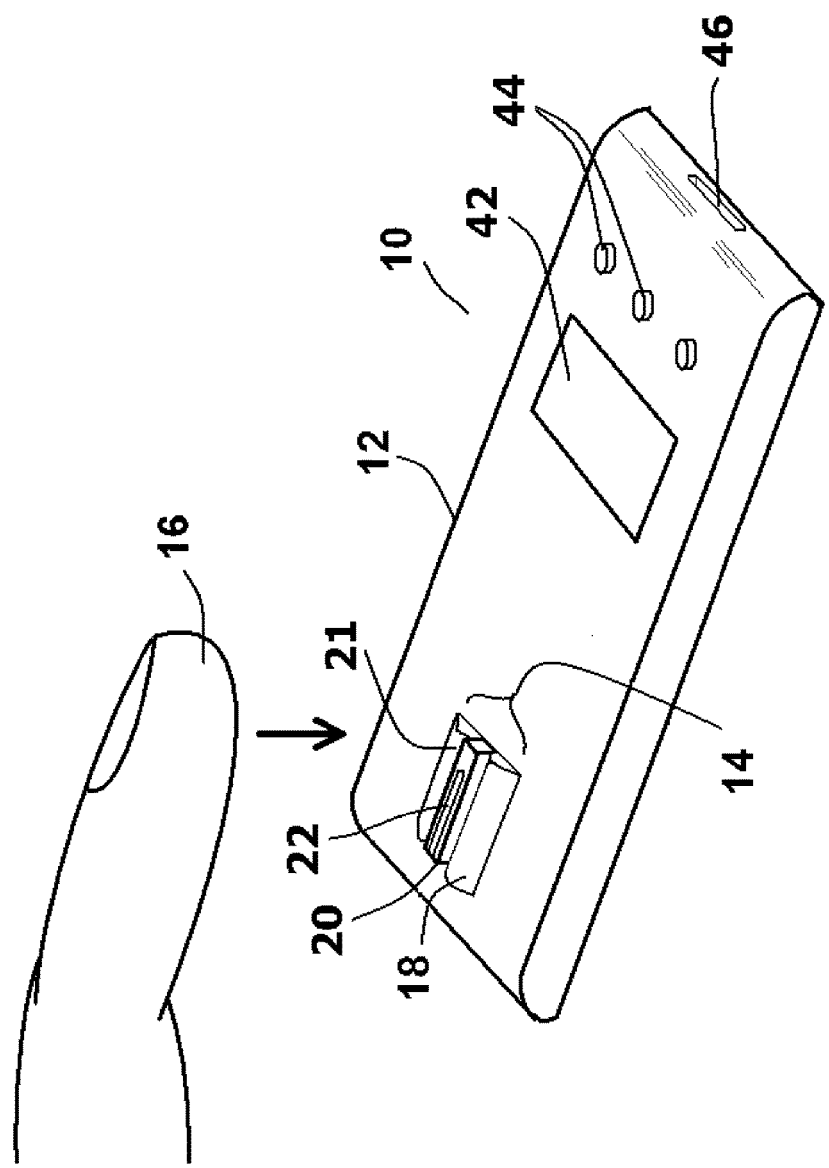
FIG. 1 shows a perspective view of an exemplary embodiment of a blood glucose monitor.
Figure 2:
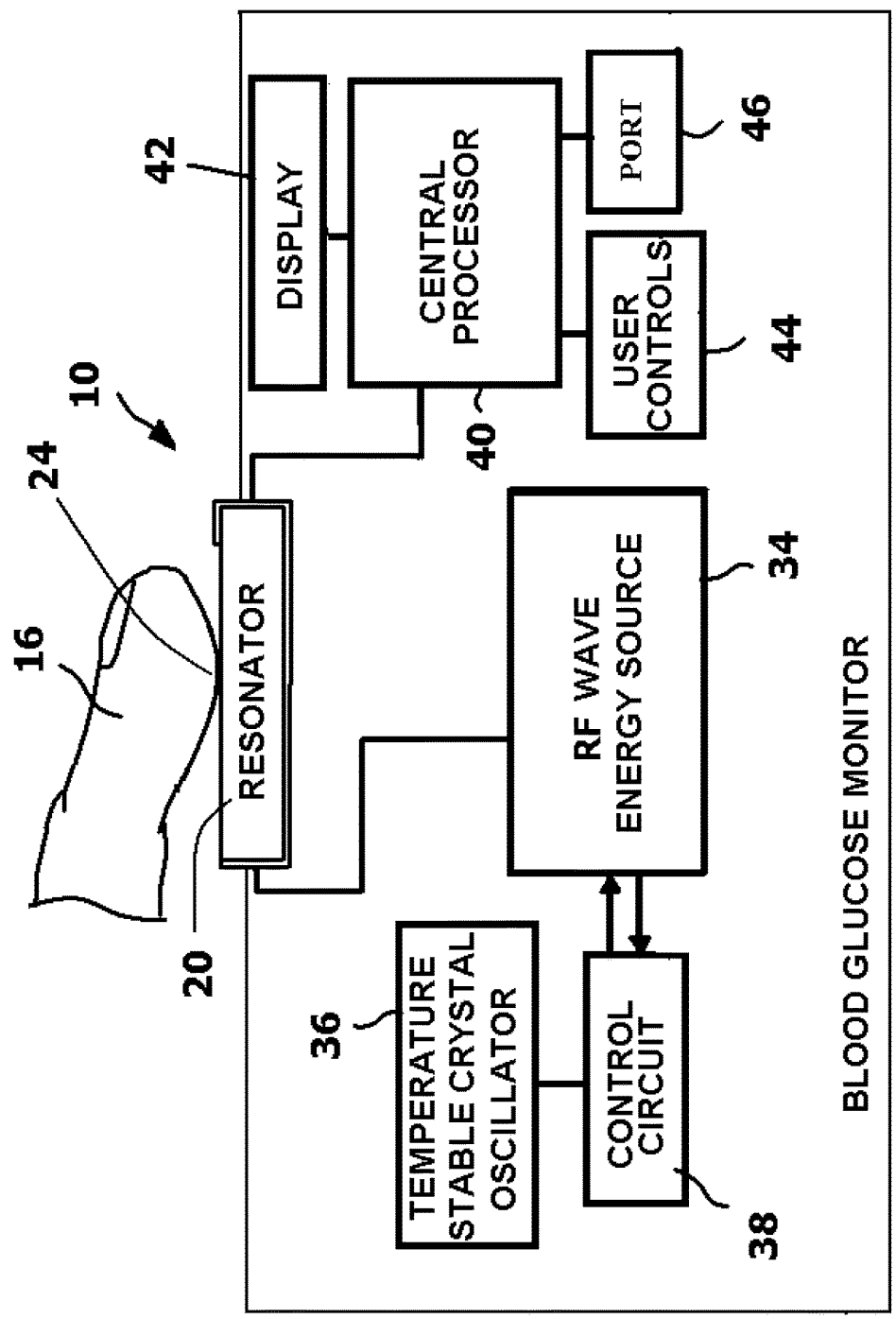
FIG. 2 is a block diagram schematic illustrating the functional components of the present invention blood glucose monitor.

Referring to FIG. 1 in conjunction with FIG. 2, a blood glucose monitor 10 is illustrated. The blood glucose monitor 10 is very small and can be embodied in a unit only slightly thicker than a credit card. In this manner, the blood glucose monitor 10 can be readily carried in the wallet, pocket, or purse of a diabetic.

The blood glucose monitor 10 has an interface surface 12. Positioned upon the interface surface 12 is a test structure 14 upon which a person places his/her fingertip 16 or another segment of body tissue. The test structure 14 includes a modified ceramic coaxial resonator 20 and inert supports 18 that surround the modified ceramic coaxial resonator 20. The inert supports 18 ensure that the modified ceramic coaxial resonator 20 is protected from lateral contact that may dislodge or otherwise damage the electrical and waveguide connections that lead to the modified ceramic coaxial resonator 20. The test structure 14 has an open top 21 that exposes the top surface 22 of the modified ceramic coaxial resonator 20. The modified ceramic coaxial resonator 20 can be very small and has a preferred length of less than 1.5 centimeters and a preferred width of less than 0.5 centimeters. As such, the open top 21 need only be a few square millimeters in area, and can a variety of shapes. In this manner, the open top 21 is far smaller than the average person's fingertip. Accordingly, if a person were to place his/her fingertip 16 or another segment of body tissue over the open top 21, the body tissue would easily cover the open top 21 and the tissue would contact the top surface 22 of the modified ceramic coaxial resonator 20.

The dimensions of the modified coaxial resonator 20 regulate its frequency of oscillation. The modified coaxial resonator 20 is sized in relation to the RF source frequency being used so that the RF source frequency is a quarter wavelength, or a multiple of the quarter wavelength, of the resonance frequency of the modified coaxial resonator 20.

The portion of the body tissue that physically touches the top surface 22 of the modified ceramic coaxial resonator 20 is considered the test sample for the blood glucose monitor 10. Since only a small portion of a person's fingertip 16 touches the modified ceramic coaxial resonator 20, it will be understood that the size of a person's fingertip 16 does not matter. Rather, regardless of whether the user is large or small, thin or fat, the test sample that actually touches the modified ceramic coaxial resonator 20 remains relatively constant. Microwave frequencies around 1 GHz penetrate the body by a few centimeters. In the present invention, microwave power levels of only 1 mW are needed. As such, the microwave exposure is low-power and non-ionizing.

The modified ceramic coaxial resonator 20 has a high degree of temperature stability at the frequency of oscillation. However, in requirements where temperature stability requirements are very high, a second similar resonator can be incorporated as a reference and circuits can be designed to negate any difference in temperature.

In FIG. 2, the small amount of body tissue that touches the modified ceramic coaxial resonator 20 is shown as the sample tissue 24. The sample tissue 24 consists primarily of skin, behind which is blood and muscle tissue. As has been previously stated, the size of the sample tissue 24 remains very consistence across a wide patient population. The sample tissue 24 touches the top surface 22 of the modified ceramic coaxial resonator 20.

Figure 3:
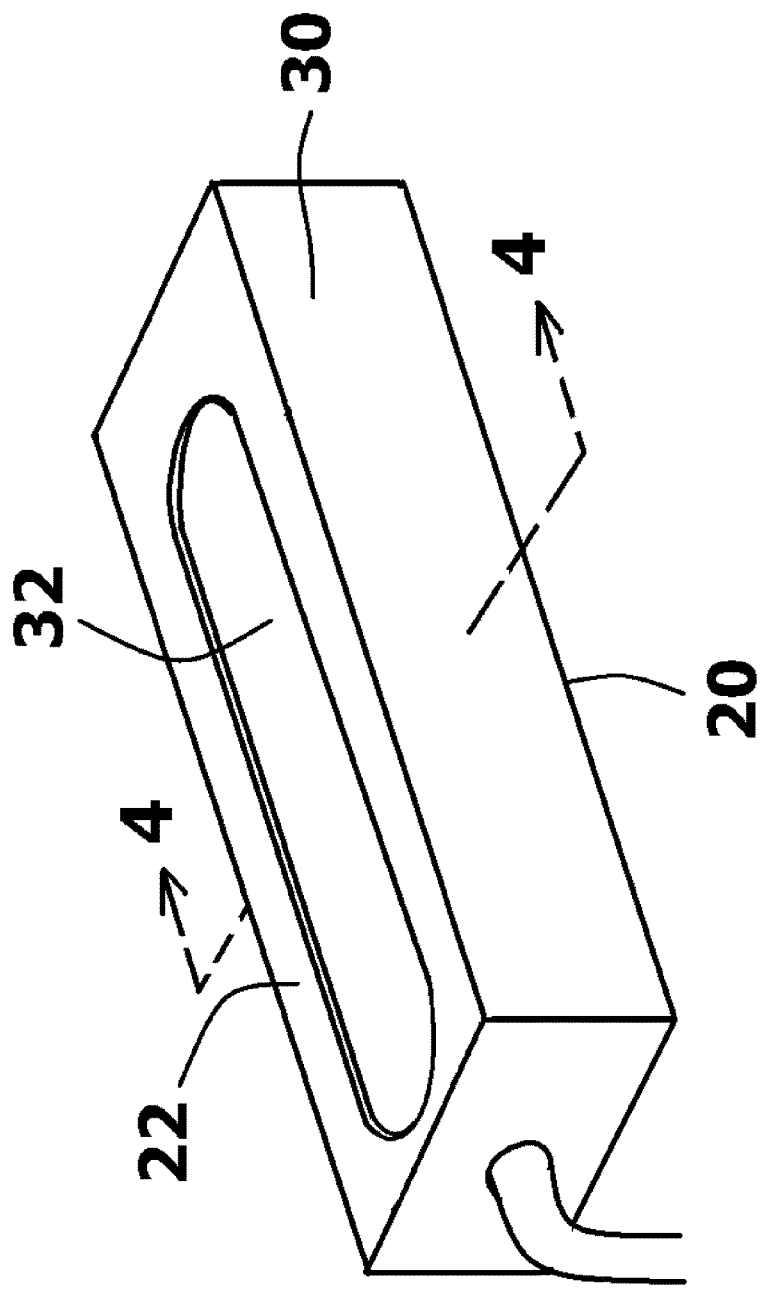
FIG. 3 is a perspective view of a modified ceramic coaxial resonator utilized by the present invention blood glucose monitor.
Figure 4:
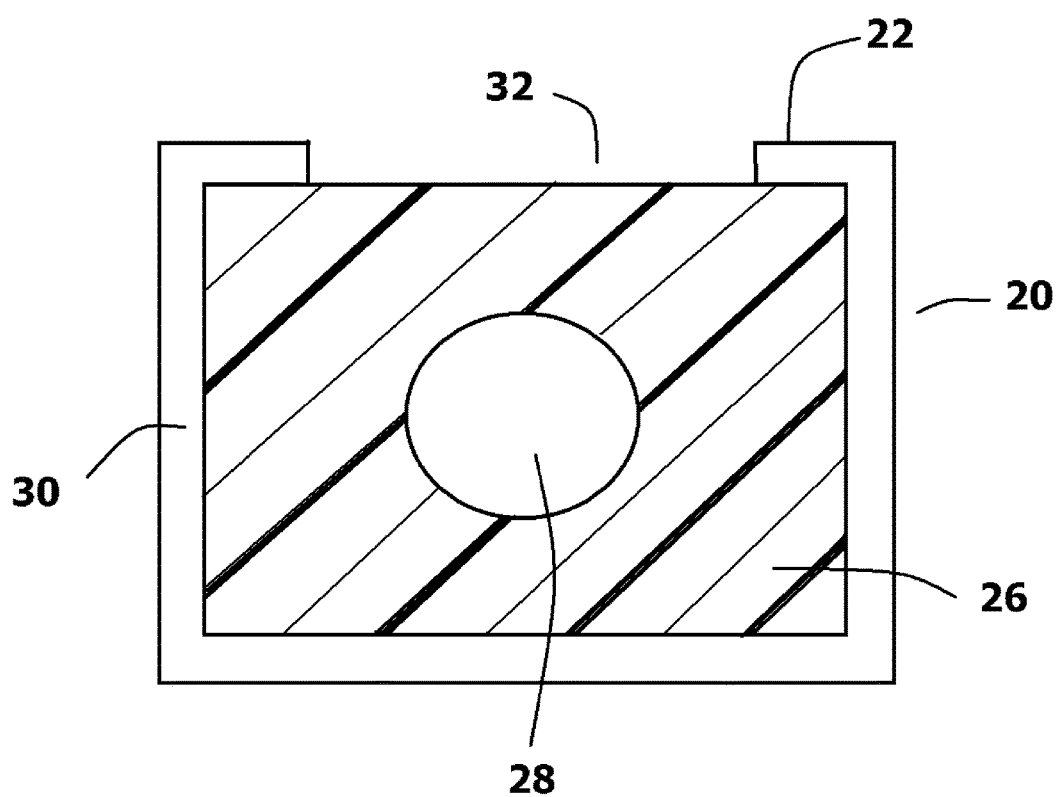
FIG. 4 is a cross-section of the embodiment of FIG. 3 vied along section line 4-4.

Referring to FIG. 3 and FIG. 4 in conjunction with FIG. 2, it can be seen that a first embodiment of a modified ceramic coaxial resonator 20 is shown that has a rectangular structure with a ceramic dielectric body 26. An inner hollow 28 extends through the ceramic dielectric body 26. The exterior of the ceramic dielectric body 26 is covered with a conductive sheathing 30, such as a plating of a silver alloy. On the top surface 22 of the modified ceramic coaxial resonator 20, the conductive sheathing 30 is removed along a slot 32. As such, the ceramic dielectric material 26 is directly exposed within the slot 32. When the sample tissue 24 touches the top surface 22 of the modified ceramic coaxial resonator 20, the sample tissue 24 contacts the slot 32 and contacts the exposed ceramic dielectric material 26 that is exposed by the slot 32. Consequently, the sample tissue 24 is not shielded by the conductive sheathing 30. As such, the sample tissue 24 is exposed to the electromagnetic fields created by the modified ceramic coaxial resonator 20.

Figure 6:
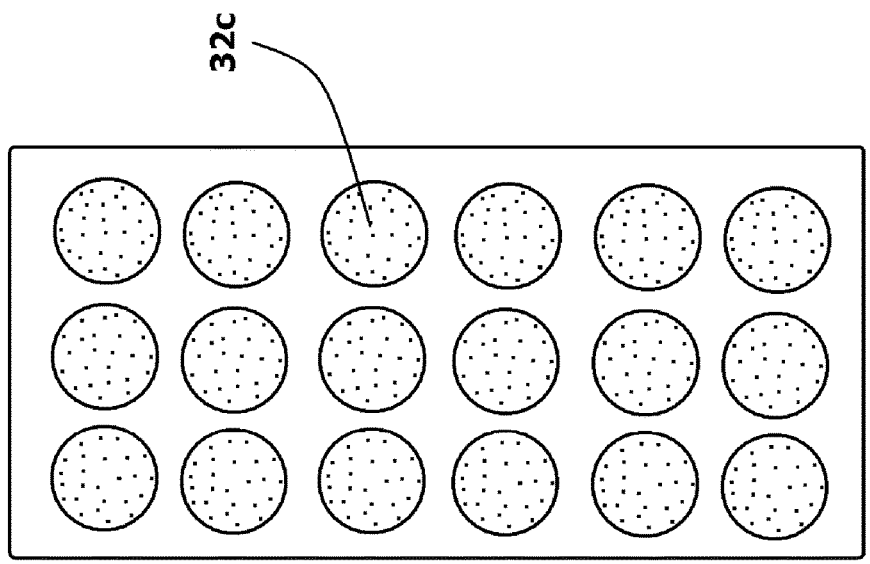
FIG. 6 is a top view of a second alternate embodiment of a modified ceramic coaxial resonator.
Figure 5:
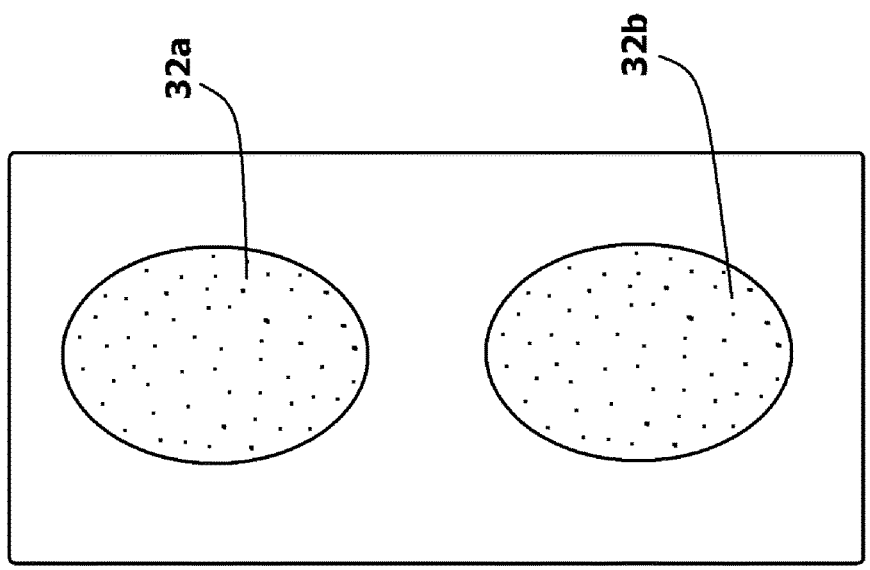
FIG. 5 is a top view of a first alternate embodiment of a modified ceramic coaxial resonator.

The dimensions of the slot 32 are not as important as its exposed area. Many different shaped slots can be used. Slots of generally equal area will provide similar results. In FIGS. 3 and 4, a single oblong the slot 32 is used. This single slot 32 can have a variety of peripheral shapes. Likewise, as is shown in FIG. 5, the exposed area can be contained in two separate slots 32a, 32b that have a combined area equal to that of the single slot 32 in FIG. 3. Likewise, as is indicated in FIG. 6 a matrix of exposed slots 32c can be provided.

Returning to FIG. 2 and FIG. 3, it will be understood that regardless to the shape and number of exposed slots on the modified ceramic coaxial resonator 20, a wave energy source 34 emits wave energy into the modified ceramic coaxial resonator 20. The modified ceramic coaxial resonator 20 produces an oscillation frequency from the wave energy that is dependent upon the bias potential and the physical characteristics of the modified ceramic coaxial resonator 20. In the preferred embodiment, wave frequencies in the ISM (Instrument, Scientific and Medical) bands are used. Preferably, the wave energy source 34 is a high Q factor microwave source. Such a microwave source provides a very stable (UHF) signal within environmental conditions. However, a millimeter wave (EHF) transmitter can also be used effectively.

The wave energy source 34 uses a temperature stable crystal oscillator 36 in a phase locked loop, and an emission control circuit 38 to ensure that the wave energy source 34 provides a stable frequency regardless of changes in temperature, humidity, and battery strength.

The dimensions of the modified ceramic coaxial resonator 20 are known, as is the resonance frequency it normally produces when not in contact with a secondary object. Consequently, when nothing touches the slot 32 on the modified ceramic coaxial resonator 20, the oscillation frequency produced remains essentially constant. However, when the sample tissue 24 touches the slot 32 on the modified ceramic coaxial resonator 20, the presence of the sample tissue 24 loads the modified ceramic coaxial resonator 20 and changes the oscillation frequency. As has been previously stated, the sample tissue 24 consists primarily of skin and blood. The skin has a fairly consistent dielectric constant that varies very little from day to day and person to person. However, it has been found that the effect of the blood on the oscillation frequency of the modified ceramic coaxial resonator 20 is significant. The dielectric constant of the blood can vary between 30 and 74 depending upon the wave frequency being used. Of the many components contained in human blood, it has been discovered that the level of glucose contained in the blood has a significant effect on the dielectric constant attributed to that blood. Other blood chemistry elements, such as iron, tend to be constant in most individuals.

Since contributing elements to the dielectric constant of the sample tissue 24, such as skin and non-glucose blood chemistries, tend to be constant in any one diabetic patient, the changes in the oscillation frequency created by these elements can be considered constant background noise and can be electronically filtered. What is left is a variation in the oscillation frequency that is caused primarily by the glucose level of the blood flowing through the sample tissue 24. The changes in the oscillation frequency are significant enough to detect changes in blood glucose levels corresponding to at least one milligram per deciliter. This level of accuracy mimics that of traditional glucometers that test drawn blood samples.

The oscillation frequency of the modified ceramic coaxial resonator 20 is detected in a traditional manner, wherein the oscillation frequency corresponds to an analog signal. The analog signal is processed by a central processing unit 40 and is converted into a voltage signal. The voltage signal is shown as a number on a display 42 on the interface surface 12 of the blood glucose monitor 10. The change of frequency into voltage can be accomplished by means of digital phase locked loop, analog phase locked loop or frequency discriminators in the control circuitry.

The central processing unit 40 is also connected to user controls 44 on the interface surface 12 of the blood glucose monitor 10. The user controls 44 include an on/off control as well as input controls that enable a user to calibrate the blood glucose monitor 10 as well as initiate various preprogrammed subroutines.

An optional computer port 46 may also be coupled to the central processing unit 40. The computer port 46 allows the central processing unit 40 to download data and/or upload data from an outside computer. In place of a physical computer port 46, the system may transmit and receive data via BlueTooth, WiFi and other wireless communication techniques.

The blood glucose monitor 10 is initially calibrated at the factory using blood samples from diabetic patients which are analyzed both by blood laboratories and by measurements using the blood glucose monitor 10. A calibration correlation is conducted and stored in an EEPROM or similar memory device within the control circuitry.

Figure 7:
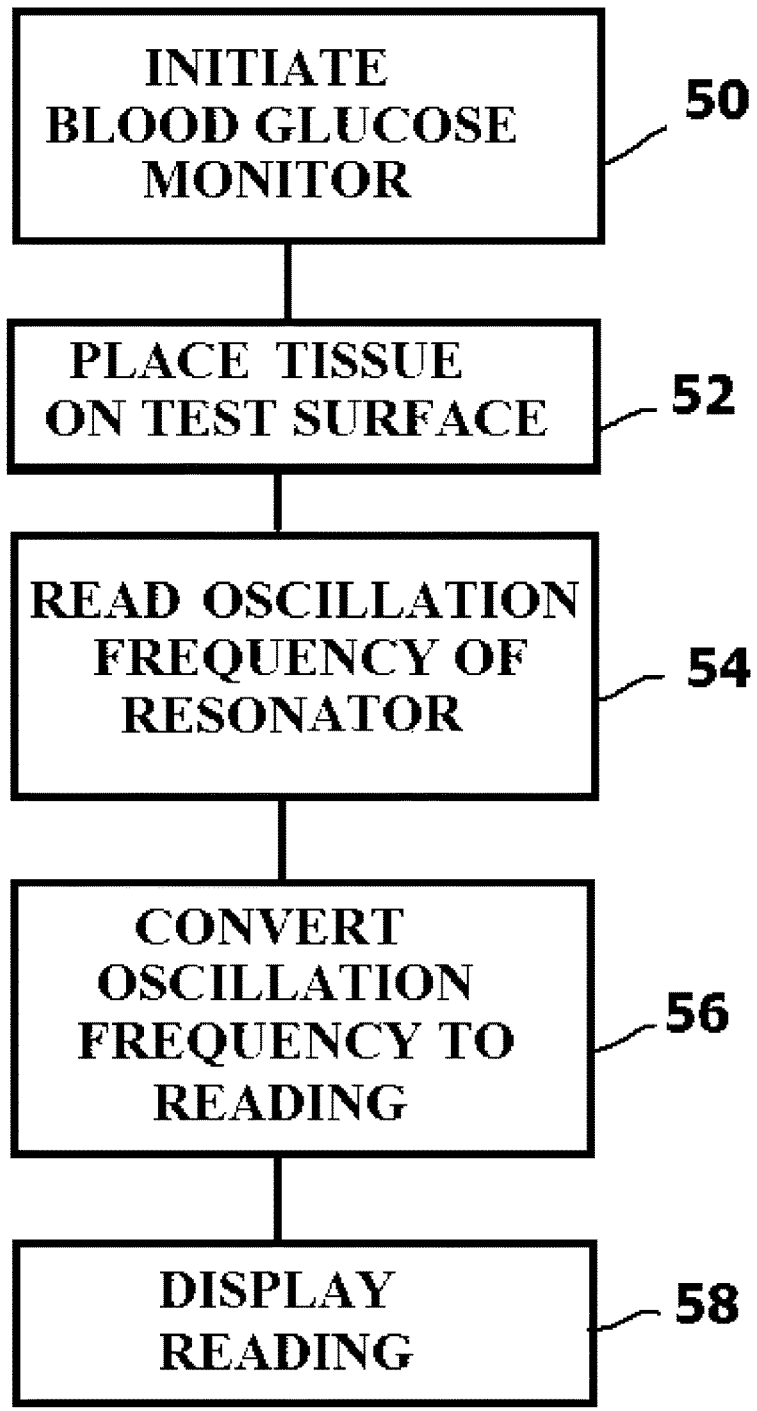
FIG. 7 is a block flow diagram illustrating the methodology of performing a test using the present invention blood glucose monitor.

Referring now to FIG. 7 in conjunction with FIG. 2, the method of operating the blood glucose monitor 10 is explained. As is indicated by Block 50, a user initiates the blood glucose monitor 10 by pressing the appropriate user control 44. Once initialized, a user places a tissue sample 24 over the slot 32 atop the modified ceramic coaxial resonator 20. See Block 52. The blood glucose monitor 10 automatically conducts a test by seeing how the sample tissue 24 touching the slot 32 affects the oscillation frequency produced by the modified ceramic coaxial resonator 20. See Block 54. The changed oscillation frequency is converted into a numerical display signal, which is presented on the display 42. See Blocks 56 and 58. The entire test sequence should take less than ten seconds. The glucose test monitor 10, therefore, enables users to test their blood glucose levels many times a day without having to draw blood samples.

Figure 8:
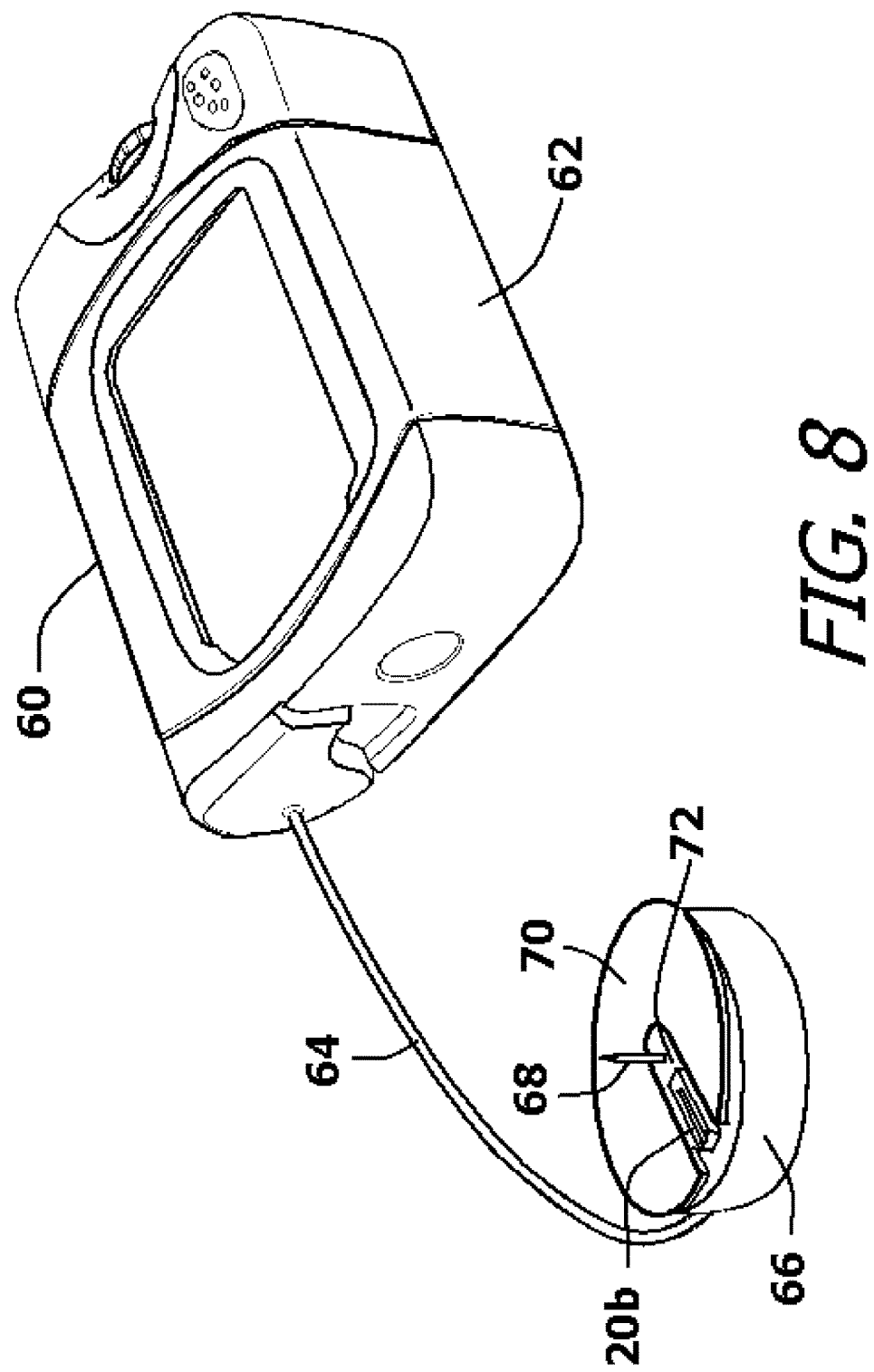
FIG. 8 is an exemplary view of an insulin pump assembly containing the present invention blood glucose monitor.

Referring to FIG. 8, an alternate embodiment of the present invention glucose test monitor is shown. In this embodiment, the glucose test monitor of the present invention is integrated into the hardware and software of an insulin pump 60. The insulin pump 60 has a primary unit 62 that is worn on the belt. The primary unit 62 contains stores of insulin, a pump and the various electronics needed for operation. A tether 64 of tubes and wires runs to an injection head 66. The injection head 66 has a needle 68 that pierces the skin and enables insulin to be injected into the patient. The injection head 66 is held onto the skin of the patient with an adhesive pad 70.

The insulin pump 60 is modified. A relief 72 is formed in the adhesive pad 70 of the injection head 66. Under the relief 72 is positioned a modified ceramic coaxial resonator 20b. When the injection head 66 is attached to a person's skin, the modified ceramic coaxial resonator 20b is brought into contact with the skin. The modified ceramic coaxial resonator 20b can then monitor blood sugar levels in the manner previously described. The blood sugar levels being read are utilized by the primary unit 62 of the insulin pump. If blood sugar levels are high, then the insulin pump 60 will inject the appropriate dose of insulin. If sugar levels are low, the insulin pump 60 will refrain from injecting insulin.

The use of the modified ceramic coaxial resonator 20b, therefore, enables the insulin pump 60 to become self monitoring. This makes the insulin pump 60 more effective and less likely to cause insulin overdoses.

Figure 9:
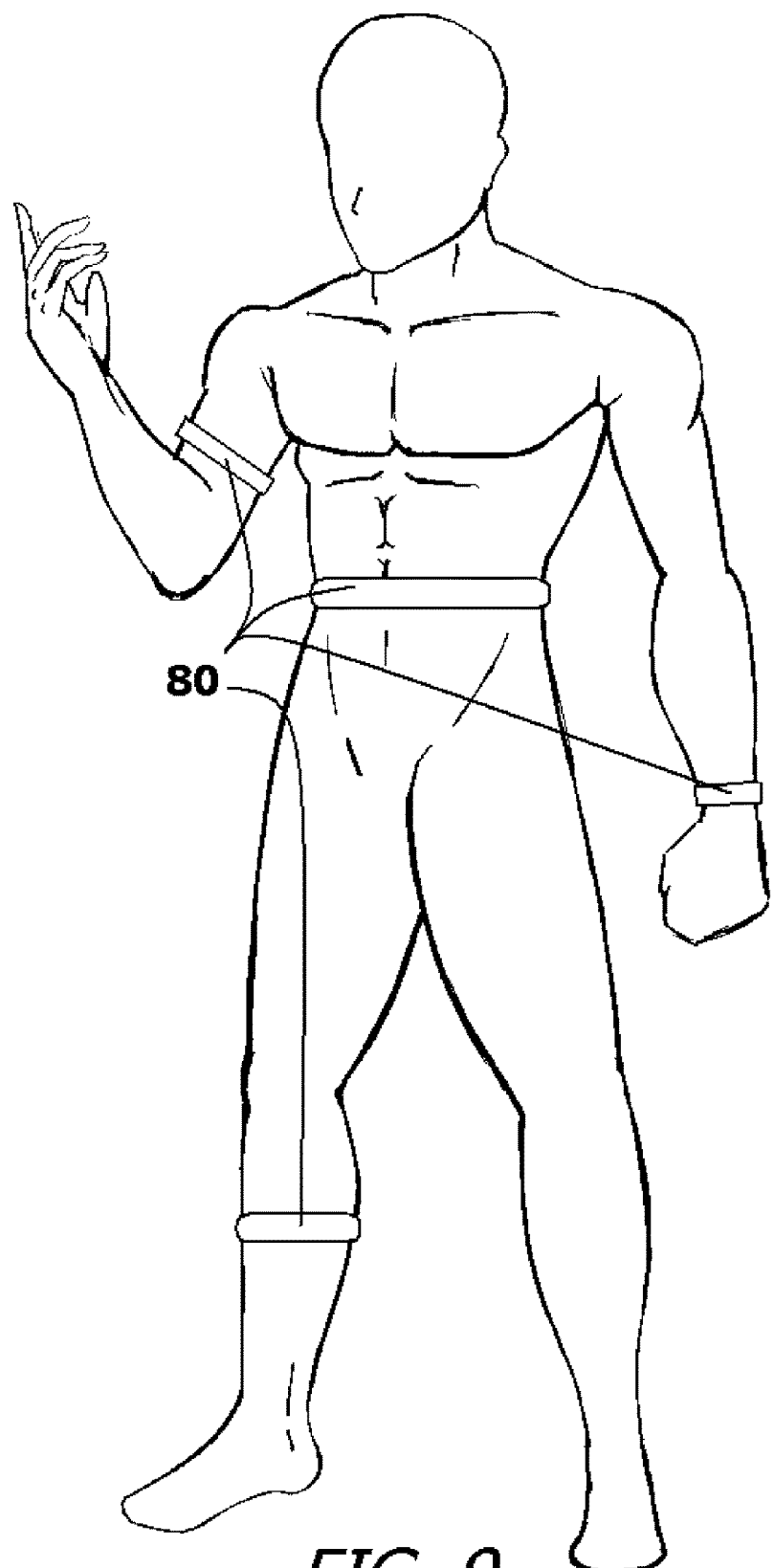
FIG. 9 shows a body with straps that illustrates positions on the body where the present invention blood glucose monitor can be attached.

In addition to being used in conjunction with an insulin pump, the present invention can be used as simply as a continuous glucose monitoring system. As us indicated in FIG. 9, the system can have a strap 80 that holds the system against the user's skin. The area of the skin is not of much importance. As such, the system can be worn around the leg, the arm, or the torso.

Figure 10:
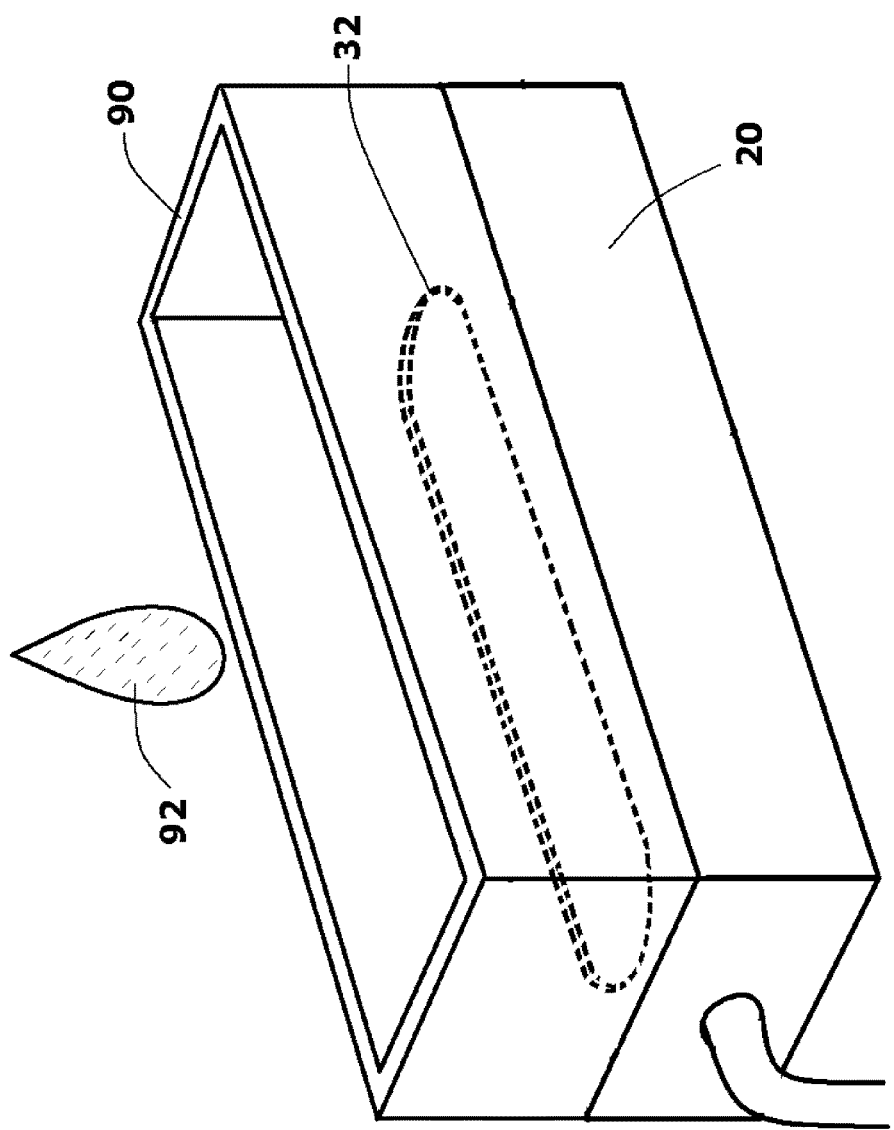
FIG. 10 shows an alternate embodiment of the modified ceramic coaxial resonator adapted to receive and analyze a liquid sample.

It will also be understood that the present invention glucose monitoring system can be used to test glucose in material other than blood-rich body tissue. Referring to FIG. 10, it can be seen that a small receptacle 90 can be built over the slot 32 in the modified ceramic coaxial resonator 20. The receptacle 90 is preferably made of quartz and is capable of holding a small volume of liquid 92, such as urine saliva or blood. The presence of the liquid will affect the resonance frequency of the modified ceramic coaxial resonator 20 in the same manner as has been previously described.

It will be understood that the embodiments of the present invention that are illustrated and described are merely exemplary and that a person skilled in the art can make many variations to those embodiments. For instance, the overall shape of the blood glucose monitor and/or insulin pump are a matter of design choice. All such embodiments are intended to be included within the scope of the present invention as defined by the claims.

What is claimed is:

1. A monitoring system for detecting glucose levels in tissue, comprising:
   a modified ceramic coaxial resonator having a central hollow surrounded by dielectric material, wherein said dielectric material is covered with a conductive material, and wherein a slot is formed in said conductive material that exposes said dielectric material;
   a wave energy source coupled to said modified ceramic coaxial resonator that causes said modified ceramic coaxial resonator to produce a frequency oscillation, and wherein contact of said dielectric material exposed in said slot with said tissue alters said frequency oscillation in correlation to glucose levels in said tissue; and
   circuitry that converts said frequency oscillation into a display signal.

2. The system according to claim 1, further including inert supports that are positioned adjacent said modified ceramic coaxial resonator and protect said modified ceramic coaxial resonator from lateral contact.

3. The method according to claim 1, wherein said wave energy source emits wave energy in bands selected from the group consisting of Instrument, Scientific and Medical (ISM) bands, microwave bands and extremely high frequency (EHF) bands.

4. The system according to claim 1, further including a display for displaying said display signal.

5. The system according to claim 1, wherein said modified ceramic coaxial resonator has a contact surface against which said tissue makes contact, wherein said slot is disposed on said contact surface.

6. The system according to claim 1, wherein said contact surface of said modified ceramic coaxial resonator has an area no greater than 1.5 square centimeters.

7. The system according to claim 1, wherein said wave energy source is a high Q microwave source.

8. The system according to claim 1, wherein said modified ceramic coaxial resonator is embodied in an injection head of an insulin pump.

9. A monitoring system for passively detecting glucose levels through skin, comprising:
   a modified ceramic coaxial resonator having dielectric material that is covered with a conductive material, wherein said modified ceramic coaxial resonator has a skin contact surface where a slot is formed in said conductive material that exposes said dielectric material;
   a wave energy source coupled to said modified ceramic coaxial resonator that causes said modified ceramic coaxial resonator to produce a frequency oscillation, and wherein contact of said dielectric material exposed in said slot with said skin alters said frequency oscillation in correlation to glucose levels in a blood supply to said skin; and
   circuitry that converts said frequency oscillation into a display signal.

10. The system according to claim 9, further including a display for displaying said display signal.

11. The system according to claim 9, further including inert supports that are positioned adjacent said modified ceramic coaxial resonator and protect said modified ceramic coaxial resonator from lateral contact.

12. The system according to claim 9, wherein said wave energy source emits wave energy in bands selected from the group consisting of Instrument, Scientific and Medical (ISM) bands, microwave bands and extremely high frequency (EHF) bands.

13. The system according to claim 9, wherein said skin contact surface of said modified ceramic coaxial resonator has an area no greater than 1.5 square centimeters.

14. The system according to claim 9, wherein said wave energy source is a high Q microwave source.

15. The system according to claim 9, wherein said modified ceramic coaxial resonator is embodied in an injection head of an insulin pump.

16. A non-invasive method for measuring blood glucose levels through a sample of body tissue, said method comprising the steps of:
   providing a coaxial resonator that has an oscillating frequency in response to an energy wave input, wherein said coaxial resonator has a conductive exterior material and an exposed strip that lacks said conductive exterior material;
   contacting the body tissue with said exposed strip, wherein said body tissue alters said oscillating frequency;
   providing a circuit that converts said oscillating frequency into a blood glucose reading; and
   displaying said blood glucose reading.

17. The method according to claim 16, further including the step of embodying said coaxial resonator and said circuit in a portable handheld device.

18. The method according to claim 16, wherein said energy wave input has a band selected from the group consisting of Instrument, Scientific and Medical (ISM) bands, microwave bands and extremely high frequency (EHF) bands.

* * * * *